United States Patent [19]

Marcus

[11] Patent Number: 5,060,639

[45] Date of Patent: Oct. 29, 1991

[54] BACK SUPPORT

[75] Inventor: Donna Marcus, Port Vue, Pa.

[73] Assignee: Helen A. Siudyla, Pittsburgh, Pa.

[21] Appl. No.: 472,846

[22] Filed: Jan. 31, 1990

[51] Int. Cl.⁵ .............................. A61F 5/00; A61F 5/03
[52] U.S. Cl. .................................... 128/78; 128/95.1;
   128/96.1; 128/101.1; 128/112.1; 2/44
[58] Field of Search .................. 128/75, 78, 95.1, 96.1,
   128/99.1, 100.1, 101.1, 112.1, 113.1, 116.1,
   117.1, 120.11; 2/44

[56] References Cited

U.S. PATENT DOCUMENTS

| | | |
|---|---|---|
| 2,250,267 | 7/1941 | Lins . |
| 2,719,973 | 2/1953 | Blatt .................... 128/96.1 |
| 3,154,072 | 1/1963 | Mack .................... 128/78 |
| 3,315,670 | 4/1967 | Fumea . |
| 3,526,221 | 9/1970 | Garber .................. 128/99.1 |
| 4,508,110 | 4/1985 | Modglin ................. 2/44 |
| 4,592,342 | 6/1986 | Salmasian .............. 128/96.1 |
| 4,616,639 | 10/1986 | Huber . |
| 4,627,109 | 12/1986 | Carabelli et al. . |
| 4,768,499 | 9/1988 | Kemp . |
| 4,789,372 | 12/1988 | Wicks . |
| 4,794,916 | 1/1989 | Porterfield et al. . |
| 4,833,730 | 5/1989 | Nelson . |

Primary Examiner—Richard J. Apley
Assistant Examiner—Lynne A. Reichard
Attorney, Agent, or Firm—Amster, Rothstein & Ebenstein

[57] ABSTRACT

A back support adapted to be worn about a person's waist comprises a resiliently compressible, flexible elongate back pad, a pair of resiliently compressible, flexible elongate side pads, and resiliently elastic, flexible strap means. The back pad and side pads are configured and dimensioned to be positioned against the wearer's lower back and sides, respectively, when the back support is worn. The back pad is filled with a resiliently compressible, flexible filler (such as foam) and has stitching therethrough which compresses the filler in different areas to different degrees. Each of the side pads is attached at one end to a respective end of the back pad. The strap means releasably connects the side pads together to adjustably fit the back support about the wearer's waist.

24 Claims, 9 Drawing Sheets

BACK SUPPORT

BACKGROUND OF THE INVENTION

The present invention relates to back supports and, more particularly, to a back support such as a sacrolumbar support adapted to be worn about a person's waist.

A commonly prescribed remedy for periodic or chronic backache is the use of a support adapted to be worn about a person's waist to alleviate the strain on the back and, in particular, on the sacrolumbar region of the back. However, none of the known back supports have been found to be totally satisfactory.

More particularly, the human back is not only concavely curved in the sacrolumbar region, but requires different levels of support (i.e., firmness) in different areas. The conventional back support having a flat surface to be pressed against the wearer's back or even a single radius of curvature therein fails to provide a desirably high level of conforming contact between the surface of the back support and the back of the wearer. The conventional low level of conforming contact frequently results in the back support riding up or down (i.e., becoming displaced) from its proper position on the wearer's back, with resultant discomfort and loss of therapeutic effect. Further, the conventional back support does not provide differing levels of support to different areas along the longitudinal axis of the sacrolumbar region so that each area receives the most therapeutic level of support for that particular area. The concave shape of the human lumbar vertebrae (L-1 through L-5) requires more support than the surrounding waist area.

Conventional back supports which wrap around the wearer's waist not only fail to provide desirable support for the waist, but are uncomfortable as well. To a large degree this results from the fact that waists differ in height (some people having short or narrow waists while others have long or wide waists), and vary in dimension depending on the wearer's position (i.e., whether the wearer is standing, sitting or lying down). This is especially noticeable when the wearer is lying on his side and the side of the back support either does not provide sufficient support for the wearer's back because the waist portion of the back support does not fully extend between the wearer's side and the mattress as necessary to provide support for the spine or is too bulky in the region between the wearer's side and the mattress so that the spine is displaced from the desirable plane parallel to the mattress.

Back problems are particularly common in pregnant women and people of either sex who have large protruding abdomens, the support of which places a strain on the sacrolumbar portion of the back. Yet the conventional back supports which wrap around a person's abdomen are not only uncomfortable for the person with the protruding abdomen to wear, but may be unhealthy as well due to the pressure applied to the protruding abdomen. Additionaly, the conventional back support does not provide both a desirable support of the protruding abdomen from below and a desirable stabilization of the protruding abdomen which keeps it properly positioned rather than flopping from side to side as the wearer turns.

Accordingly, it is an object of the present invention to provide a back support which is adapted to closely conform to the wearer's sacrolumbar region and provide the varying levels of firmness desirable for each respective area thereof.

Another object is to provide such a back support having side portions which are easily modifiable by the wearer to provide a desired bulkiness for the particular wearer and the particular position of the wearer at given time.

A further object is to provide a back support which is not only useful to and comfortable for wearers having protruding abdomens (such as pregnant women) but also provides support and stabilization for the protruding abdomen.

SUMMARY OF THE INVENTION

It has now been found that the above and related objects of the present invention are obtained in a back support adapted to be worn about a person's waist comprising a resiliently compressible, flexible elongate back pad, a pair of resiliently compressible, flexible elongate side pads, and flexible strap means. The back pad and side pads are configured and dimensioned to be positioned against the wearer's lower back and sides, respectively, when the back support is worn. The back pad is filled with a resiliently compressible, flexible filler material and has stitching therethrough which compresses the filler material in different areas to different degrees. Each of the side pads is attached at one end to a respective end of the back pad. The strap means releasably operably connects the side pads together to adjustably fit the back support, about the wearer's waist.

In a preferred embodiment, the stitching defines first areas of greater stiffness adjacent each side of the back pad and at least one second area of lesser stiffness intermediate the first areas so that the back Pad has greater thickness and less firmness in the second area and less thickness and greater firmness in the first areas. Typically the stitching defines a plurality of second areas of lesser stiffness intermediate the first areas. The back pad includes a fabric cover about the filler material which is preferably substantially homogeneous foam. The back pad has an egg crate inner surface facing away from the wearer and a generally smooth outer surface facing the wearer.

The back support additionally includes at least one loop disposed on each side pad intermediate the ends thereof for adjusting the bulk of the side pad to fill the portion of the wearer's waist intermediate the rib cage and the hips and thereby provide support thereto when the wearer lies on his/her side on a generally flat surface. Each of the loops is removable from its respective side pad, slidable along the length of its respective side pad for adjusting the distribution of the bulk thereof, and/or elastic.

In an embodiment of the back support expressly adapted to be worn about the waist of a wearer who is pregnant or otherwise possessed of a protruding abdomen, the strap means is bifurcated into an upper portion and a lower portion, so that the strap means may be disposed to the top and bottom of the protruding abdomen of the wearer. The lower portion of the strap means is configured and dimensioned to at least Partially support the protruding abdomen, and the upper portion of the strap means is configured and dimensioned to stabilize the position of the protruding abdomen. The back support may additionally including a resiliently elastic cover extending between and connecting the upper and lower portions of the strap means.

The strap means may be side fastening——i.e., fixedly or removably secured at one end thereof to the other end of one of the side pads and removably secured at the other end thereof to the other end of the other one of the side pads for releasably connecting the strap means and the other one side pad adjacent the side of the wearer to adjustably fit the back support about the wearer's waist. Alternatively, the strap means may be front fastening——i.e., comprise a pair of strap elements, each strap element being secured at one end thereof to the other end of a respective one of the side pads and having fastening means at the other end thereof for releasably connecting the strap elements together to adjustably fit the back support about the wearer's waist.

The back support is preferably of unitary one-piece construction, and the strap means is preferably resiliently elastic.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
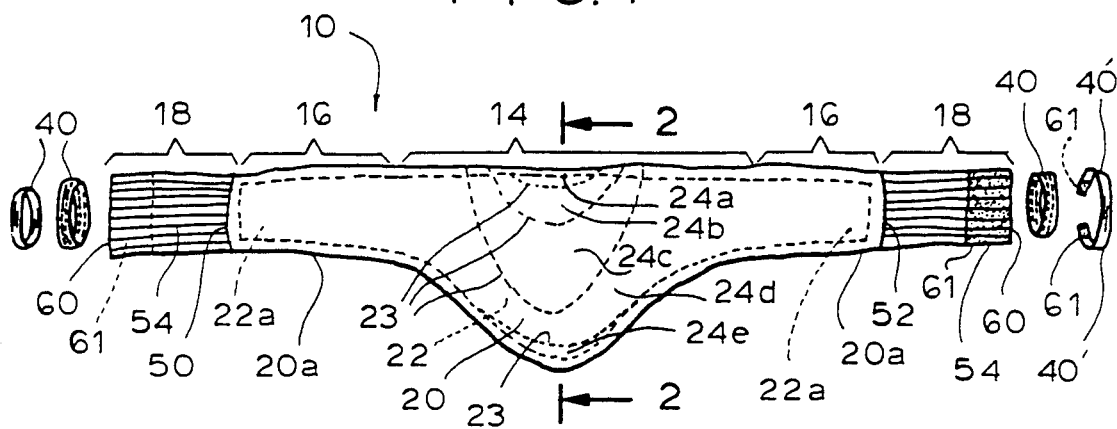
FIG. 1 is an exploded front elevational view of a back support according to the present invention.
Figure 2:
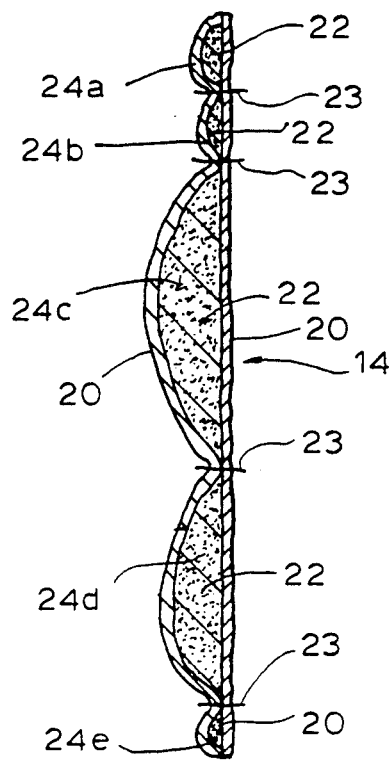
FIG. 2 is a sectional view of the back support, to an enlarged scale, taken along the line 2—2 of FIG. 1.
Figure 3:
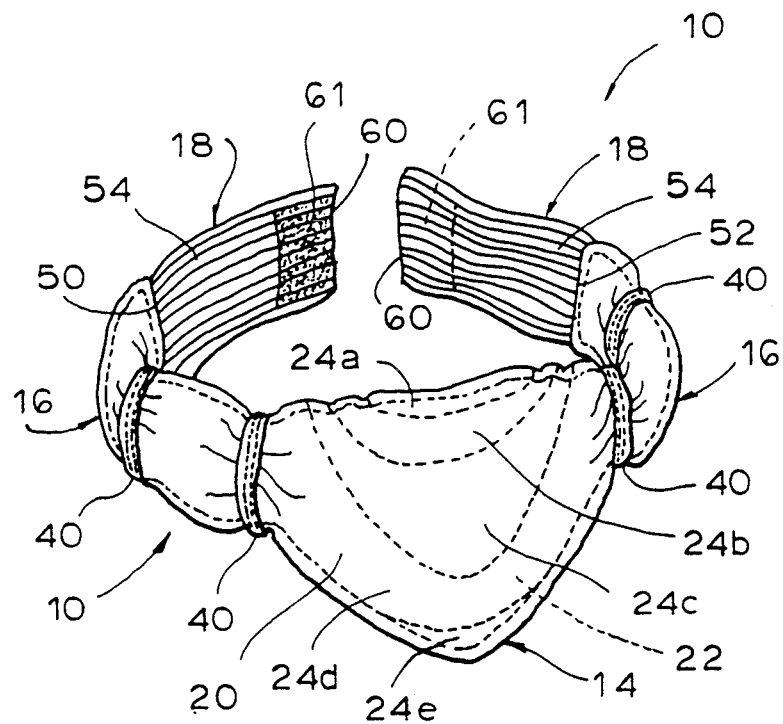
FIG. 3 is an isometric view of the back support from the rear thereof.
Figure 4:
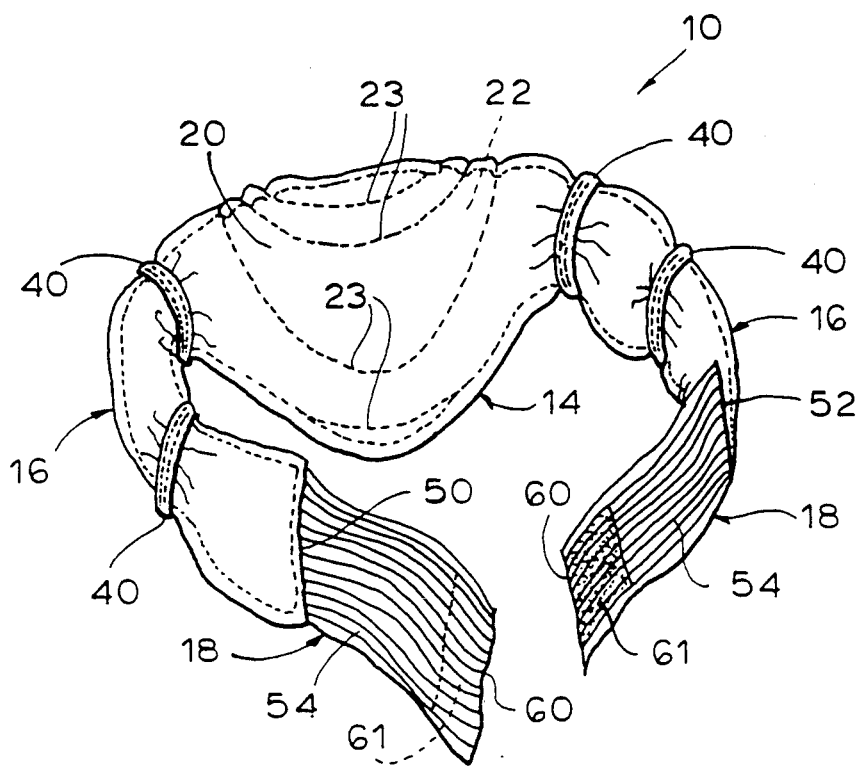
FIG. 4 is an isometric view of the back support from the front thereof.
Figures 5, 6:
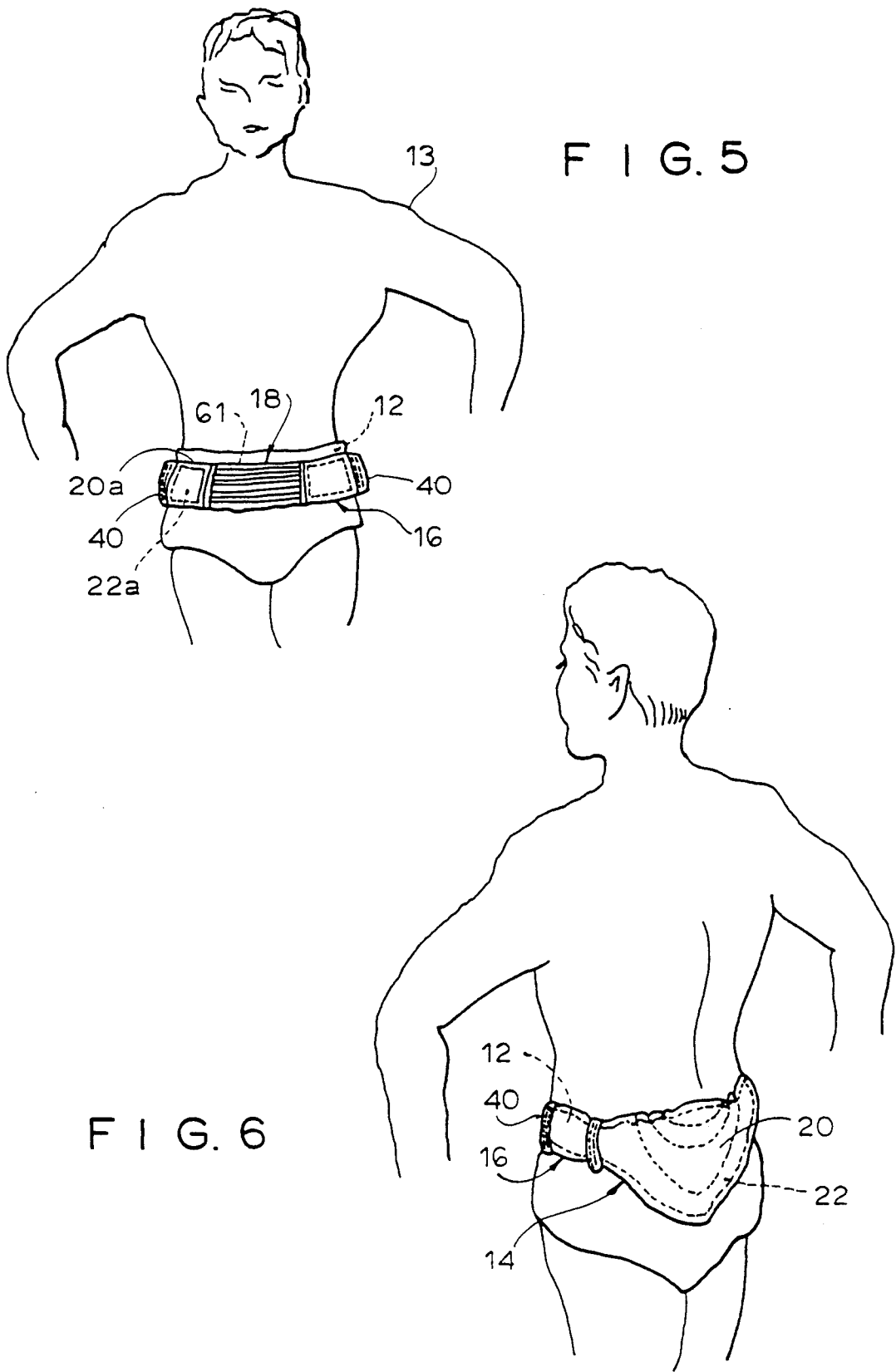
FIG. 5 is a fragmentary front elevational view of a man wearing the back support.
FIG. 6 is a fragmentary back elevational view of a man wearing the back support.
Figure 7:
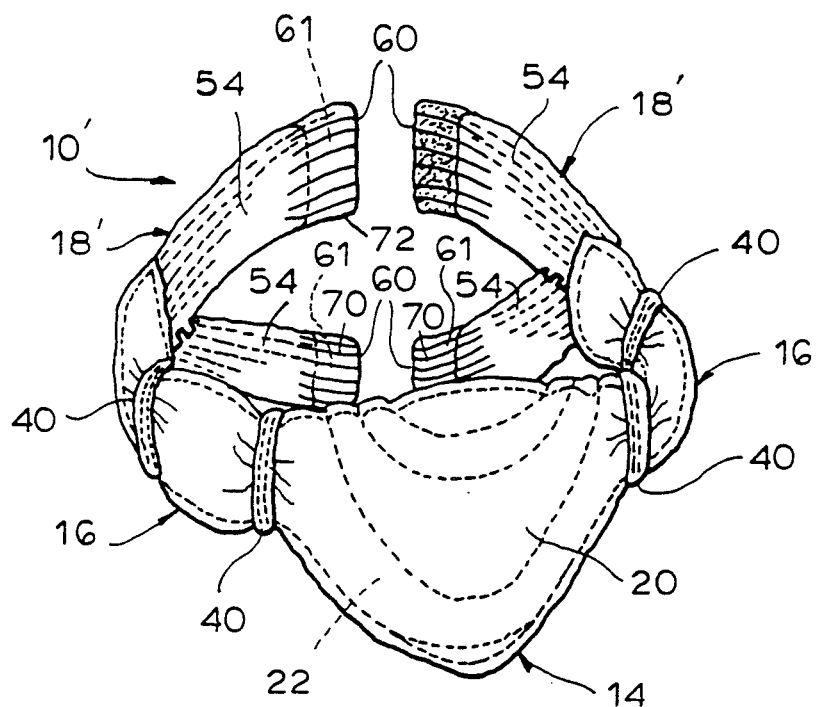
FIG. 7 is an isometric view from the rear of a "pregnancy" embodiment of the back support suitable for use by a person with a protruding abdomen.
Figure 8:
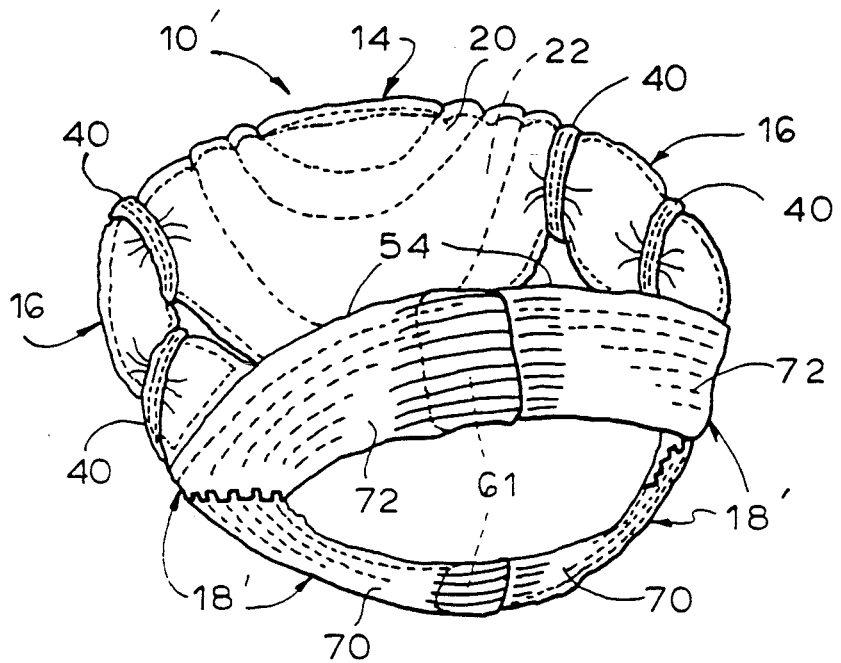
FIG. 8 is an isometric view of the pregnancy embodiment from the front thereof.
Figure 9:
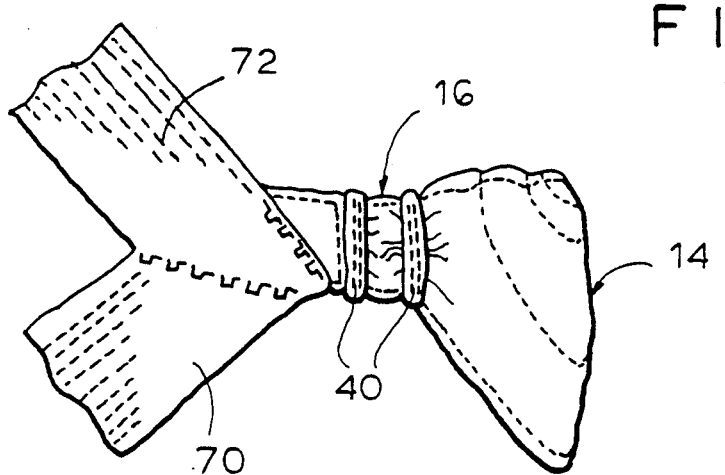
FIG. 9 is a fragmentary side elevational view of the pregnancy embodiment.
Figure 10:
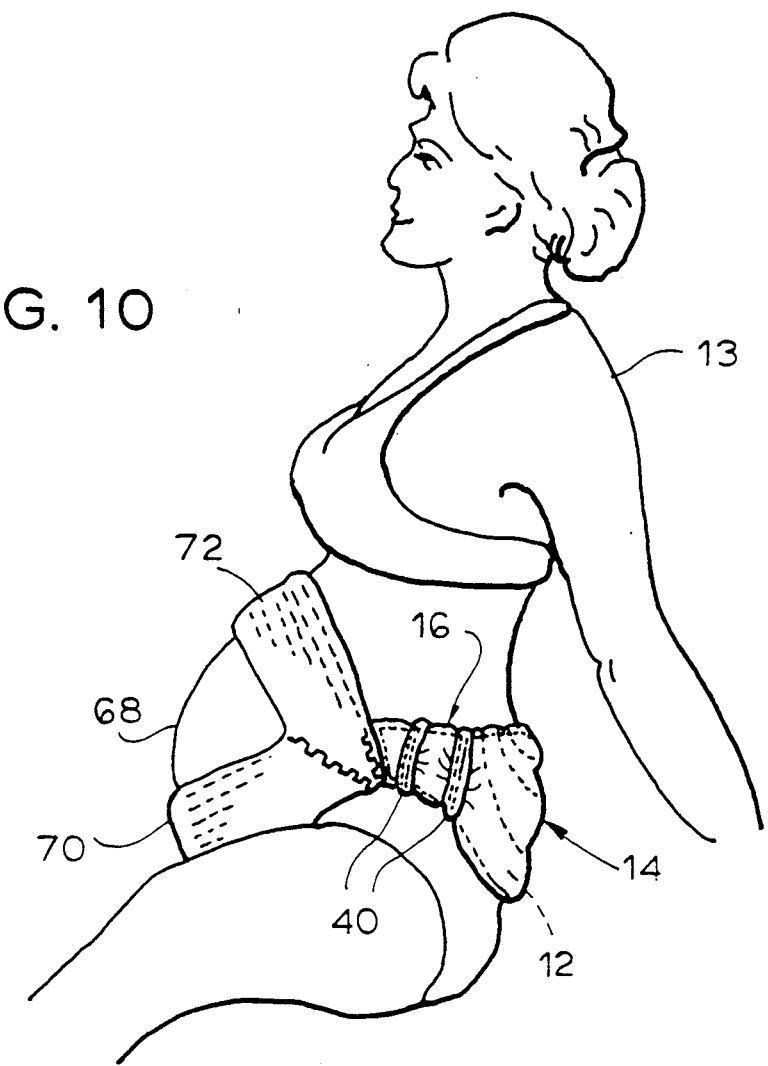
FIG. 10 is a fragmentary side elevational view of a pregnant woman wearing the pregnancy embodiment.
Figure 11:
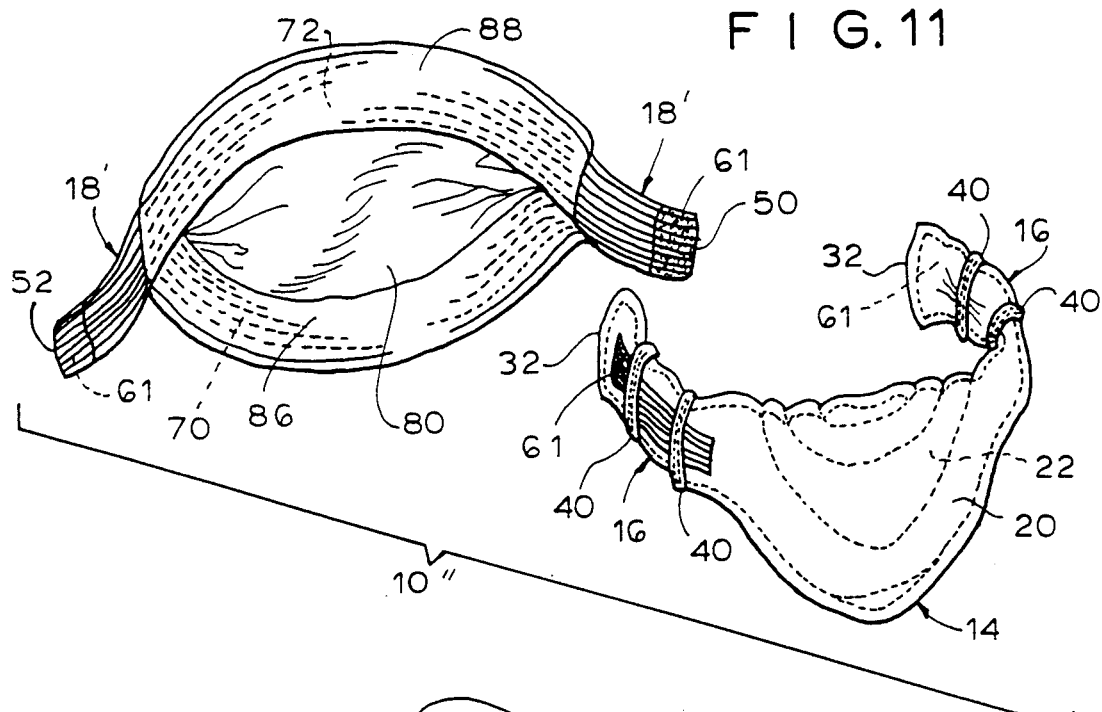
FIG. 11 is an exploded isometric view from the rear of the pregnancy embodiment with an integral cover.
Figure 15:
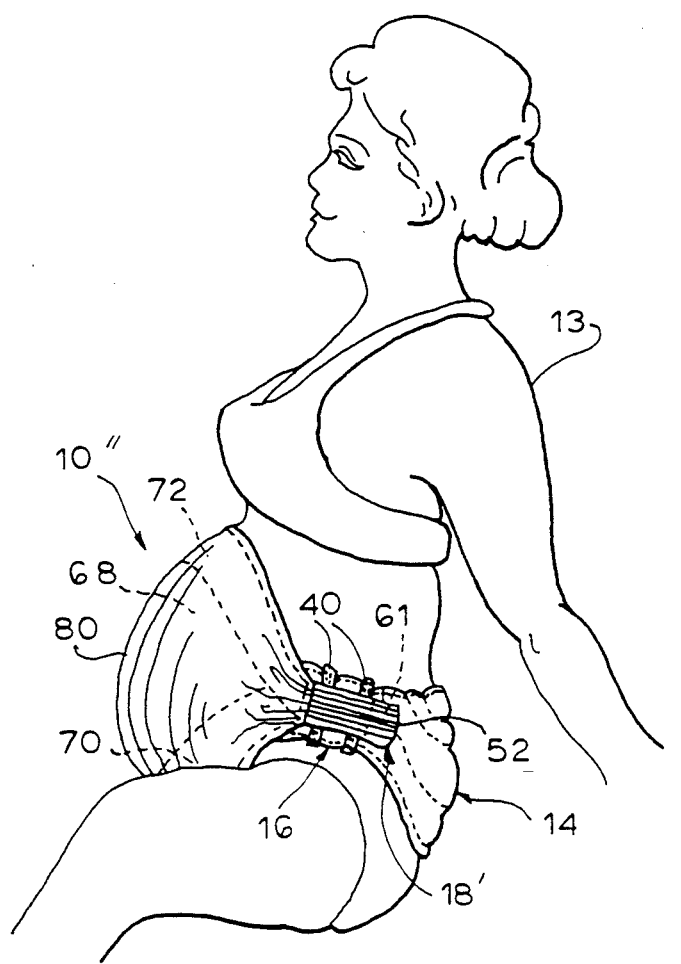
FIG. 15 is a side elevational view of a pregnant woman wearing the pregnancy embodiment with an integral cover.
Figure 12:
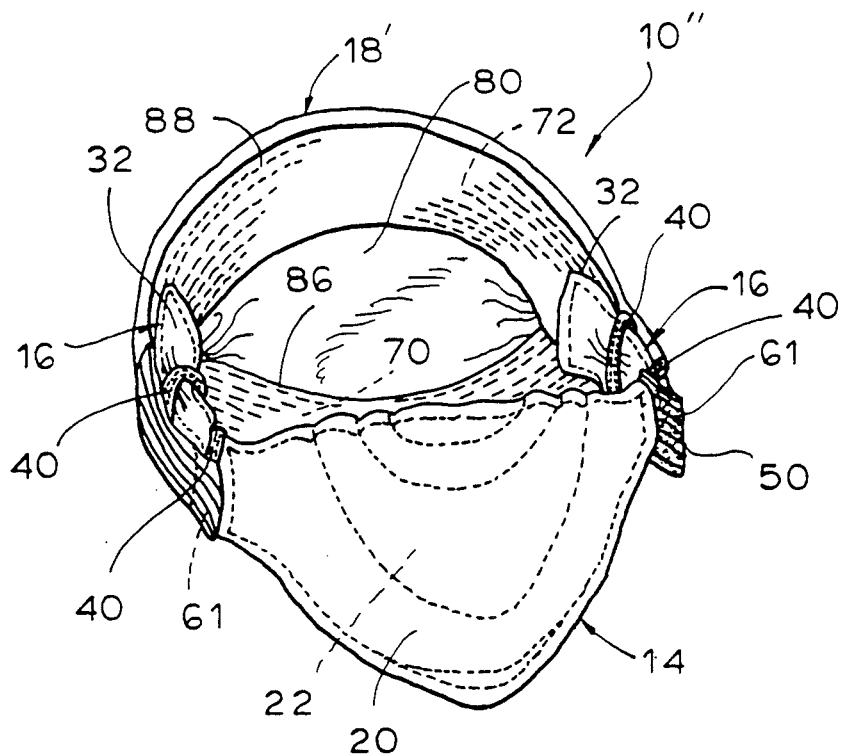
FIG. 12 is an isometric view of the pregnancy embodiment with an integral cover from the back thereof.
Figure 13:
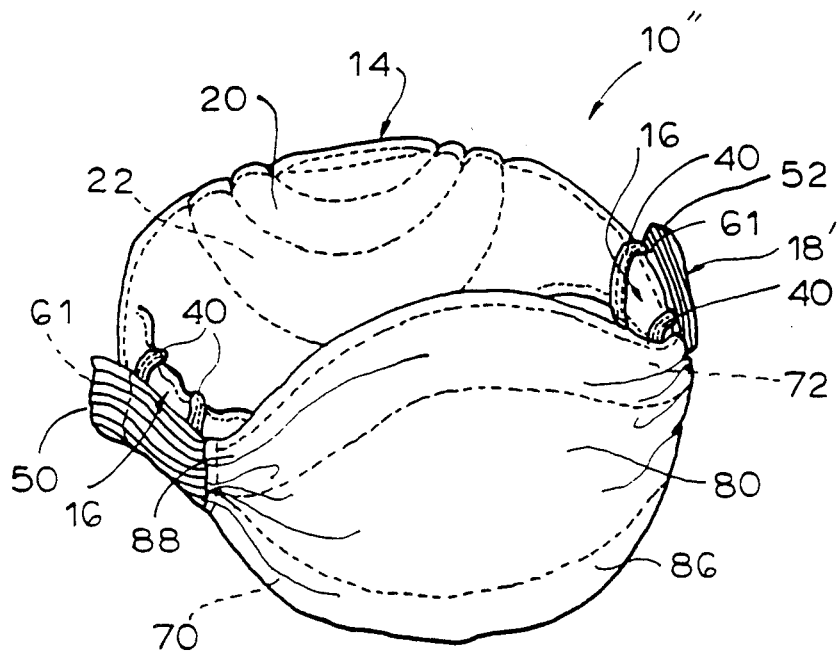
FIG. 13 is an isometric view of the pregnancy embodiment with an integral cover from the front thereof.

Referring now to the drawing, and in particular to FIGS. 1-6 thereof, therein illustrated is a back support according to the present invention, generally designated by the reference numeral 10. The back support 10 is adapted to be worn about the waist 12 of a wearer 13 (see FIGS. 5 and 6) and essentially comprises a resiliently compressible, flexible elongated back pad generally designated 14, a pair of elongate resiliently compressible, flexible elongate side pads generally designated 16, each side pad being attached at one end to a respective end of the back pad 14, and resiliently elastic, flexible strap means generally designated 18 for releasably operably connecting the side pads 16 together to adjustably fit the back support 10 about the wearer's waist 12.

More particularly, the resiliently compressible, flexible, elongate back pad 14 is configured and dimensioned to be positioned against the wearer's sacrolumbar region when the back support is worn about the person's waist 12. The back pad 14 is preferably comprised of a tubular cover 20, such as natural or synthetic fabric, which is filled with a resiliently compressible, flexible filler material 22, such as foam. The back pad 14 has stitching 23 therethrough which compresses the filler material 22 in different areas 24a, 24b, 24c, 24d, 24e along the longitudinal axis of the sacrolumbar region to different degrees. As the filler material 22 becomes more compressed as a result of the stitching, it becomes firmer (that is, provides more resistance to further compression). In a preferred embodiment, the back pad 14 has central areas 24b, 24c, which are of greater thickness (i.e., extend further horizontally into the curvature of the back) and areas 24a, same. The areas 24a, 24d, 24c of lesser thickness are more compressed by the stitching 23 and define areas of greater stiffness for those areas of the sacrolumbar region where there is less curvature; the areas 24b, 24c of greater thickness are less compressed by the stitching 23 and define areas of lesser stiffness for those areas of the sacrolumbar region where there is more curvature.

It will be appreciated that the stitching 23 effectively forms in the fabric cover 20 pockets which maintain the different portions of the filler material 22 at the appropriate levels of compression. To this end, the fabric cover 20 is preferably formed of a flexible material having a non-stretchable or limited-stretchability characteristic so that the filler-containing capacity of a pocket in a given area 24a-24e is fixed by the stitching 23. Thus, the stitching 23 defines areas 24a, 24b, 24e of greater stiffness adjacent the top and bottom of the back pad and at least one area 24c, 24d of lesser stiffness intermediate the areas of greater stiffness 24a, 24d, 24e so that the back pad 10 has areas 24b, 24c of greater firmness in the middle thereof and areas 24a, 24b, 24e of lesser firmness at the top and bottom thereof.

The foregoing applies when considering the central portion of the back support which is intermediate the ends thereof and thus aligned with the backbone during use. Preferably, however, stitching 23 and the areas 24a-24e are not in horizontal planes, but rather horizontally extending curves, especially U-shaped curves with the upper areas having shallow curves and the lower areas generally having more sharply bent U-shaped curves. Typically, although not necessarily, the areas 24a, 24b and 24c have the free ends of the legs thereof terminating at the top of the back pad 14, the bottom area 24e has the free ends thereof terminating at the bottom of the back pad 14, and the area 24d has the free ends thereof terminating at least partially at the ends of the back pad 14.

It will be appreciated that the stitching 23 of the present invention enables a homogeneous filler material 22 to provide an effect similar to that which might be obtained using a variety of different filler materials in different areas of a multi-pocket cover while at the same time affording various advantages thereover in terms of ease and economy of manufacture, resistance to shifting or displacement of the filler during use, and the like.

The back pad 14 is of a generally triangular configuration with the triangle pointing downwardly and having a generally flat top. Where further lower back support is necessary, the bottom aspect or apex of the back pad 14 may be extended downwardly into the groove between the wearer's buttocks so as to support a generally straight spine when the wearer is lying on his back. Where further upper back support is necessary, the back pad 14 may be extended upwardly in the center thereof to provide additional support and comfort to the upper portions of the back.

The filler material 22 is preferably 100% hypoallergenic foam, and may be a rubber or plastic foam. The face of the foam which will be adjacent the wearer is preferably smooth, while the opposite side is preferably ridged or egg crated to enable the foam to flexibly conform as necessary to meet the variety of body curves that may be encountered and provide a distributed pressure thereto.

Each of the resiliently compressible, flexible, elongate side pads 16 is configured and dimensioned to be positioned against a respective side of the wearer when the back support 10 is worn. Each side pad 16 extends outwardly from a respective end of the back pad 14. Each side pad 16 includes a tubular cover 20a (e.g., of fabric) with filler material 22a disposed therein (e.g., a foam). Preferably, though not necessarily, the cover 20a and filler 22a of the side pads 16 are of the same composition as the cover 20 and filler material 22 of the back pad 14. Indeed, the cover 20a of the side pads 16 is preferably of unitary integral one-piece construction with the cover 20 of the back pad 14, such an arrangement offering the advantages of ease and economy of manufacture as well as providing a more durable and aesthetic product. Alternatively, the side pads 16 may be distinct and separate entities from the back pad 14 and joined thereto either fixedly (e.g., by stitching) or removably (e.g., by hook and loop type fastenings of the type available under the tradename VELCRO).

Unlike the back pad 14, however, the side pads 16 are not stitched to define areas of differing thickness and stiffness as the varieties of contours to be encountered by a side pad defy easy anticipation or categorization. Thus, each side pad 16 is provided with at least one loop 40 disposed intermediate the ends thereof for adjusting the bulk of the side pad 16 to fill the portion of the wearer's waist intermediate the rib cage and the hips and thereby provides support thereto when the wearer lies on his/her side on a generally flat surface (such as a mattress). Each loop 40 is slidable along the length of its respective side pad 16 in order to enable adjustment of the distribution of the bulk of the side pad so that the bulk characteristics or dimensions of the side pad may be adjusted for the comfort of the wearer in different positions and to maintain the sacrolumbar region of the spine in a plane parallel to the mattress when the wearer is lying on his/her side. To this end, the loops 40 are preferably strongly resiliently elastic, exerting sufficient compressive force on the filler material 22 within the side pads 16 to modify the configuration thereof. While the presence of the loop 40 compressing the filler material about which it extends will vary the stiffness of the filler material in that area (i.e., a tighter loop making for a stiffer area), to either side of the immediate region of the loop the filler material is free to expand to its full configuration within the cover. Accordingly, the loops 40 have little effect on the overall stiffness of the side pads 16 and are primarily effective to vary the dimensions thereof to meet the contours of the wearer.

If desired, as illustrated with respect to the rightmost loop 40' of FIG. 1, the loops 40 may be removable from their respective side pads 16——for example, each loop 40 may be formed of a strip of material 44 having cooperating closure means 46 at the ends thereof to enable the strip ends to be separated for removal of the loop 40 from the side pad 16 or secured together once the loop has been placed on the side pad in its desired position along the length thereof. It will be appreciated that, where the loop 40 is removable from its side pad 16, it is not necessary that the loop be either elastic or slidable along the length of its respective side pad because the loop may simply be removed in order to appropriately position it along the length of the side pad. Preferably, the effective length of the loop 40 is variable by the user——for example, wide bands of hook and loop type fastening material 61 or a series of snap closures may be provided at the ends thereof so that the user can employ the most apt Velcro portions or snap sets to provide the desired effective length of the loop. Another advantage of a removable loop 40 is that it may be removed in order to enable the side pad 16 to more naturally conform to a generally flat (uncurved) side of the wearer. In the preferred embodiment illustrated, the loops 40 are elastic, slidable and removable.

The strap means 18 are formed of a flexible material and releasably operably connects the side pads 16 together to adjustably fit the back support 10 about the wearer's waist 12. The strap means is preferably, although not necessarily, resiliently elastic. In the front fastening form illustrated in FIGS. 1-6, the strap means 18 comprises a pair of strap elements 54, each of the strap elements being releasably or non-releasably (preferably non-releasably) secured at one end 50, 52 thereof to a respective one of the side pads 16 and having fastening means 58 adjacent the other end 60 thereof for releasably connecting the strap elements 54 together to adjustably fit the back support 10 about the wearer's waist 12. Where the strap means 18 or strap element 54 is fixedly secured to a side pad 16, the connection may be made by conventional fastening means well known to those skilled in the art, including stitching. Where the connection of the strap means 18 to the side pad 16 is releasable or for the releasable connection 58 of the strap elements 54 together, the connection may be made by conventional releasable fastening means well-known to those skilled in the art, for example, hook and loop type fastening strips 61 (one strip having a multitude of minute resilient hooks and the cooperating complementary strip having a multitude of minute loops which can be entered by the hooks). The releasable fastening means preferably provides for an adjustable connection. For example, at least one of the hook and loop type fastening strips 61 should be sufficiently wide to enable the effective closed length of the back support to be varied continuously over an anticipated range. Instead of a wide strip, however, a series of narrow strips may be provided to enable the same overall range of adjustment to be made in discrete steps.

Alternatively, in the side-fastening form illustrated in FIGS. 11-15 in connection with a modified "pregnancy" embodiment "10" of the present invention, the strap means 18' is secured adjacent one end 50 thereof to one of the side pads 16 at the end 32 thereof and is removably secured adjacent the other end 52 thereof to the other side pad 16 at the end 32 thereof for releasably connecting the strap means 18' and the other side pad 16 adjacent the side of the wearer to adjustably fit the back support 10 about the wearer's waist 12. If desired, the strap means 18' may be removably secured at both ends 50, 52 thereof to respective side pads 16 so that the strap means 18' is completely detachable from the side pads 16, as illustrated. Preferably, however, the strap means 18 is non-removably secured at one end 50, 52 to the side pad 16 so that the entire back support 10 is of unitary one-piece construction and therefore no portions thereof can become lost during washing, storage, or the like (with the possible exception of any removable loops 40).

Referring now to FIGS. 7-10, therein illustrated is a "pregnancy" embodiment 10' of the present invention expressly adapted to be worn about the waist 12 of a wearer 13 who is pregnant or otherwise possessed of a protruding abdomen or belly 68. In this embodiment 10', the central portion of strap means 18' is bifurcated into a lower portion 70 and an upper portion 72 so that the strap means 18' may be disposed both to the bottom and to the top of the protruding abdomen 68 of the wearer 13. The lower portion 70 of the strap means 18' is configured and dimensioned to at least Partially support the protruding abdomen 68, the weight of the protruding abdomen helping to support the back and the back helping to support the protruding abdomen. The upper portion 72 of the strap means 18' is configured and dimensioned to stabilize the position of the protruding abdomen 68 relative to the remainder of the wearer's trunk (e.g., to minimize sway of the protruding abdomen from side to side as the wearer turns).

The strap means 18 is illustrated in FIGS. 7-10 in the front fastening form——i.e., the form of the strap means 18' in which each lower and upper strap portion 70, 72 is composed of two separable strap elements 54. Each strap element 54 is releasably or non-releasably secured at one end 50, 52 to a respective side pad 16 and releasably fastenable together with the other side pad 16 at the other end 60. The front-fastening form is easier for the wearer 13 to put on or remove, especially at the later stages of pregnancy, as less twisting of the torso is required. Additionally, the front fastening form permits the effective length of each lower and upper strap portions 70, 72 to be individually and independently adjusted to provide the best possible fit for the wearer 13. It will be understood, however, that the strap 18' may also be in the side fastening form——i.e., the form of the strap means 18' illustrated in FIGS. 11-15 in which each lower and upper portion 70, 72 is of unitary one-piece construction, fixedly or releasably secured at one end 50, 52 to one of the side pads 16 and releasably secured at the other end 52, 50 to the other side pad 16. In the illustrated embodiment the lower and upper portions 70, 72 of the strap means 18' are joined together at each 50, 52 end so that the effective length of one strap portion 70, 72 cannot be changed relative to the effective length of the other strap portion 72, 70, although this is not the case in the embodiment of FIGS. 17 and 18 described hereinbelow.

Referring now to FIGS. 11-15, therein illustrated is a modified "pregnancy" embodiment 10" of the present invention, adapted to be worn about the waist of a wearer who is pregnant or otherwise possessed of a protruding abdomen 68, the modified embodiment including a resiliently elastic cover 80 extending between and connecting the lower and upper portions 70, 72 of the strap means 18'. The cover 80 provides an enhanced aesthetic character to the strap means 18', and hence the entire back support 10', by offering a relatively smooth front surface, so that the strap means 18' is less visible under the wearer's clothing. Additionally, it also provides an even more efficient therapeutic uplifting and stabilizing of the protruding abdomen 68. The elastic cover 80 is especially useful during the period starting with the fifth month of pregnancy in order to firmly 'support the abdomen and decrease stomach motion of the wearer.

Figure 16:
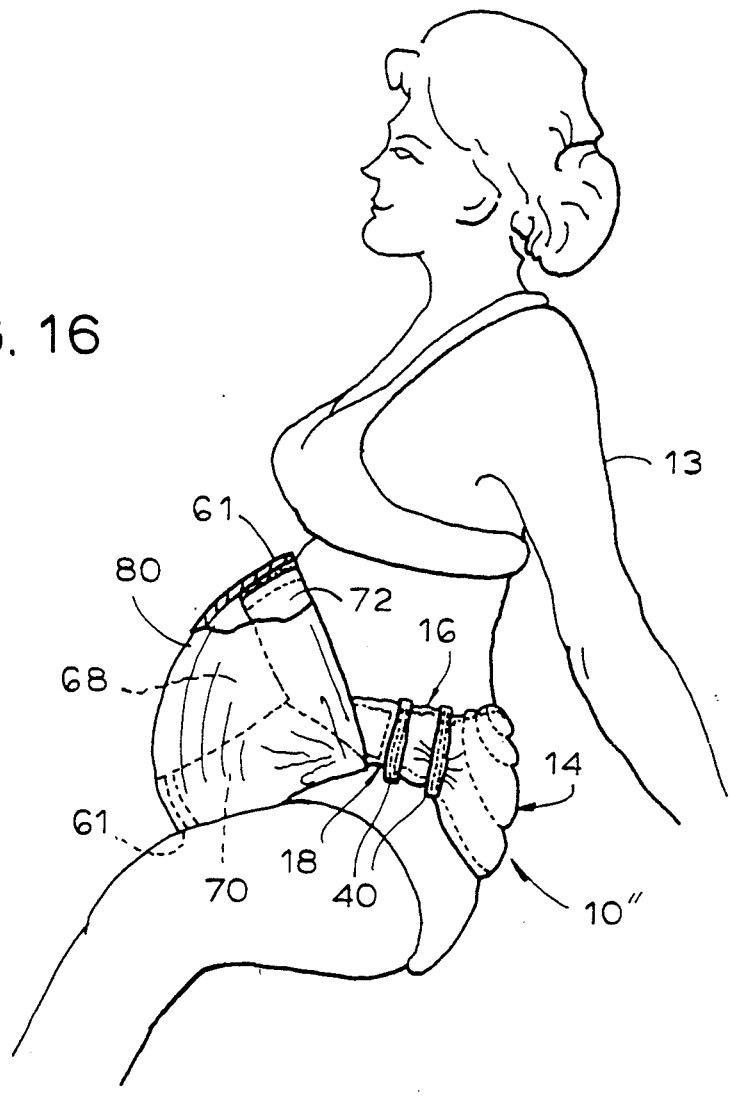
FIG. 16 is a side elevational view of a pregnant woman wearing the pregnancy embodiment with a removable cover.
Figure 14:
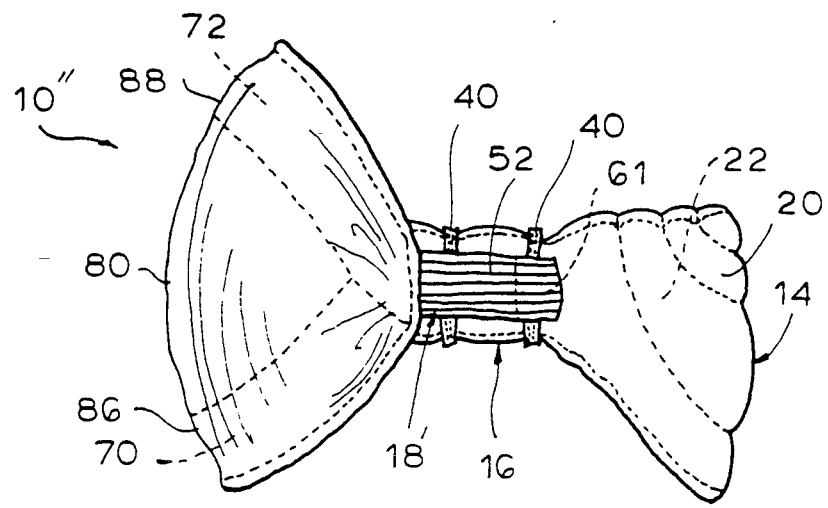
FIG. 14 is a side elevational view of the pregnancy embodiment with an integral cover.

The modified embodiment 10" may be used with the front fastening form of strap means 18', illustrated in FIG. 16, in which case the cover 80 is preferably removable from the strap means 18'. Thus, the outer peripheral surface of the lower and upper central strap portions 70, 72 (that is, the surfaces facing away from the wearer s abdomen 68) may have a hook and loop type fastening strip 61 or other releasable fastening means adapted .to interact respectively with a cooperating hook and loop type fastening strip 61 or other releasable fastening means on the lower and upper portions of the inner peripheral surface of an unpocketed cover 80 to separably integrate the cover 80 and the strap means 18'.

The modified embodiment 10" may also be used with the side fastening form of strap means 18', as illustrated in FIGS. 11-15, in which case the cover 80 is fixedly (i.e., non-removably) or removably secured thereto. Where the cover is fixedly secured to the strap means 18', the cover 80 and strap means 18' may be stitched together with the top portion of the cover being stitched to the upper strap portion 72 and the bottom portion of the cover being stitched to the lower strap portion 70. In this event, the longitudinal stretchability of the lower and upper strap portions 70, 72 and the lower and upper portions of the cover 80 is limited by the least longitudinally stretchable of the two elements 70, 72 and 80. Typically the strap means 18' is less stretchable than the cover 80. Accordingly, as, illustrated in FIGS. 11-15, preferably the lower portion of the cover 80 defines a longitudinally extending pocket 86 configured and dimensioned to receive the lower strap portion 70 therein, and the upper portion of the cover 80 defines a longitudinally extending pocket 88 configured and dimensioned to receive the upper strap portion 72 therein. This arrangement enables the cover 80 to expand or contract longitudinally (that is, along the axes of the lower and upper strap portions 70, 72) independently of the lower and upper strap portions 70, 72 as the cover pockets 86, 88 and strap portions 70, 72 are capable of relative movement. On the other hand, the ends 50, 52 of the strap means 18' do not permit complete removal of the cover 80 from the strap means 18' and thus ensure that the strap means 18' and cover 80 are kept together as a unit during cleaning and storage. Indeed, if one of the ends 50, 52 of strap means 18' is non-removably secured to one of the side pads 16, then the entire back support 10 is of unitary, integral one-piece construction so that no portions thereof (with the exception of any removable loops 40) can become separated from the remainder during cleaning or storage.

Figure 17:
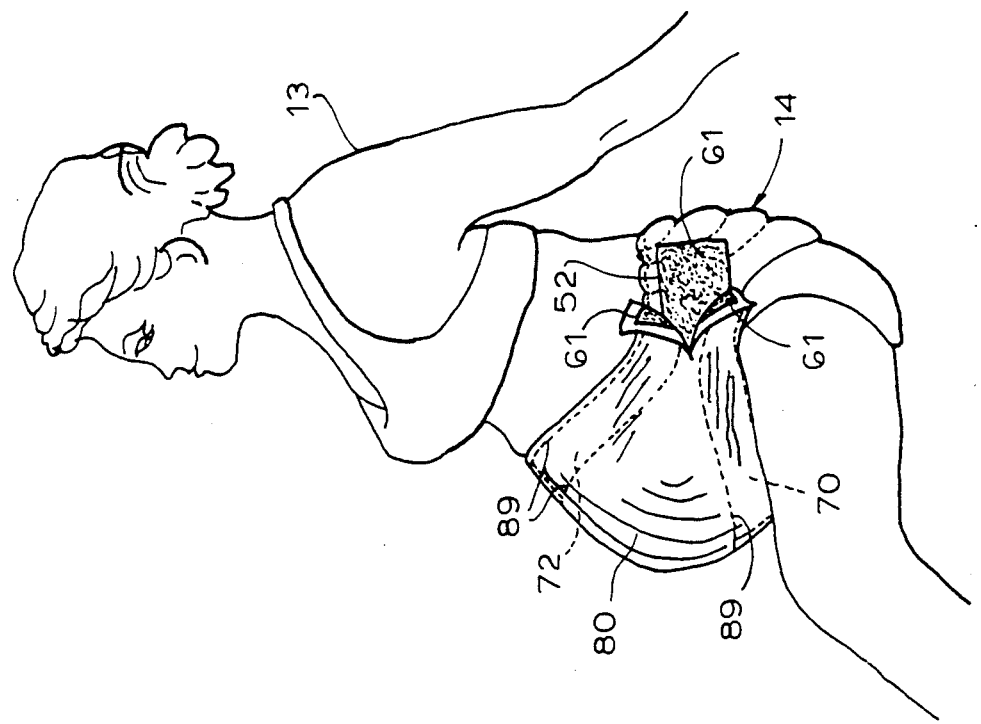
FIGS. 17 and 18 are fragmentary side elevational views of a pregnant woman wearing a pregnancy embodiment with independently adjustable lower and upper strap portions.
Figure 18:
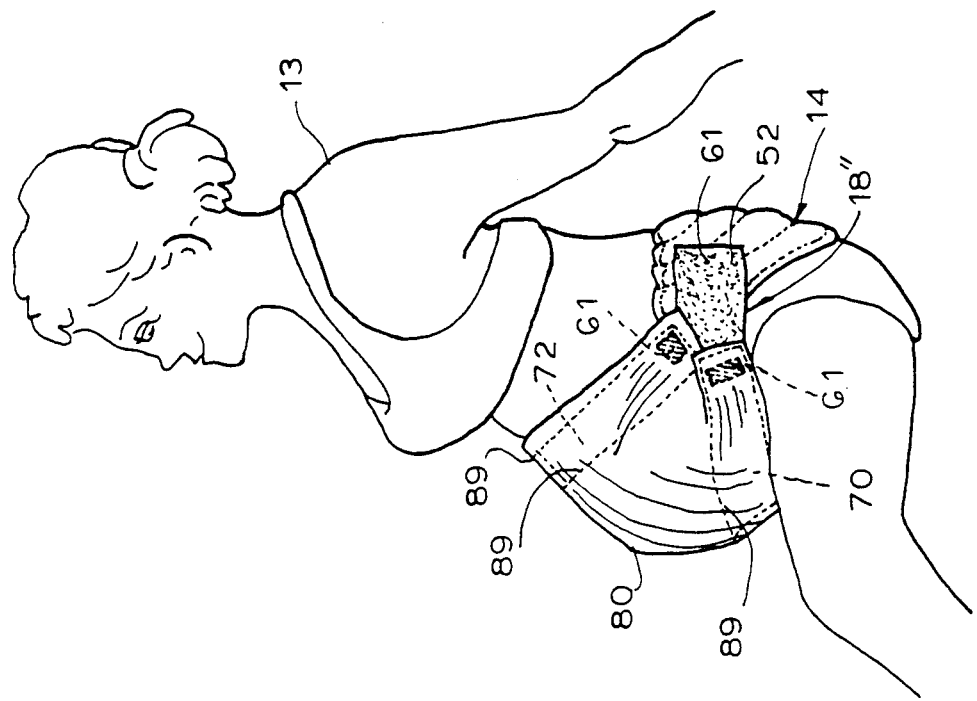

Referring now to FIGS. 17 and 18, therein illustrated is a variant of embodiment 10″ in which the cover 80 is non-removably secured to a side fastening form 18″ of the strap means——e.g., by stitching 89. At least one of the lower and upper central strap portions 70, 72 is releasably secured to at least one (and optionally both) of the strap means ends 50, 52 so that the relative positions and relative effective lengths of the lower and upper central strap portions can be independently varied within limits by appropriate placement of the one central strap portion end on the one strap means end 50, 52. Preferably, as shown, both the lower and upper central strap portions 70, 72 are so releasably secured to at least one of the strap means ends 50, 52 so that the position and effective length of each central strap portion 70, 72 may be varied. As illustrated, if desired, in this variant of embodiment 10″ the strap means ends 50, 52 may overlie and be either removably or fixedly secured to (or even serve as) the respective side pads 16, the ends 50, 52 having releasable fastening means such as a hook and loop type fastening strip 61 on the outer exposed surface thereof for engagement by the cooperating releasable fastening means such as a hook and loop type fastening strip 61 on the inner faces of the lower and upper strap portions 70, 72.

It will be appreciated that the loops 40 may be dispensed with in the various embodiments, as particularly illustrated in FIGS. 17-18.

The material of cover 80 is preferably sufficiently stretchable to allow the stomach to grow freely as the pregnancy progresses, while at the same time being sufficiently elastic to provide a desirable level of support and stabilization to the protruding abdomen.

Preferably, the entire back support is launderable and air permeable for comfort during warm weather.

To summarize, the present invention provides a back support which is adapted to closely conform to the wearer's sacrolumbar region, which provides the varying levels of firmness desirable for each respective area thereof, and which has side portions which are easily modifiable by the wearer to provide a desired bulkiness for the particular wearer and the particular position of the wearer at a given time. A special embodiment is particularly useful to and comfortable for wearers having protruding abdomens (such as pregnant women) and provides support and stabilization for the protruding abdomen.

Now that the preferred embodiments of the present invention have been shown and described in detail, various modifications and improvements thereon will become readily apparent to those skilled in the art. Accordingly, the appended claims are to be construed broadly and in a manner consistent with the spirit and scope of the invention described herein.

I claim:

1. A back support adapted to be worn about a person's waist comprising:
   (A) a resiliently compressible, flexible, elongate back pad configured and dimensioned to be positioned against the wearer's lower back when said back support is worn, said back pad being filled with a resiliently compressible, flexible filler material and having stitching therethrough which compresses said filler material in different areas to different degrees; said stitching defining first areas of greater stiffness adjacent each side of said back pad and a plurality of second areas of lesser stiffness intermediate said first areas, whereby said back pad has greater thickness and less firmness in said second areas and less thickness and greater firmness in said first areas;
   (B) a pair of resiliently compressible, flexible, elongate side pads configured and dimensioned to be positioned against the wearer's sides when said back support is worn, each of said side pads being secured at one end to a respective end of said back pad; and
   (C) flexible strap means for releasably operably connecting said side pads together to adjustable fit said back support about the wearer's waist.

2. The back support of claim 1 wherein said filler material is foam.

3. The back support of claim 1 wherein said back pad includes a fabric cover about said filler material.

4. The back support of claim 1 wherein said filler material is substantially homogeneous.

5. The back support of claim 1 wherein said back pad has an egg crate inner surface facing away from the wearer and a generally smooth outer surface facing the wearer.

6. The back support of claim 1 additionally including at least one loop disposed on each side pad intermediate the ends thereof for adjusting the bulk of said side pad to fill the portion of the wearer's waist intermediate the rib cage and the hips and thereby provide support thereto when the wearer lies on his/her side on a generally flat surface.

7. The back support of claim 6 wherein each of said loops is removable from its respective side pad.

8. The back support of claim 6 wherein each of said loops is slidable along the length of its respective side pad for adjusting the distribution of the bulk thereof.

9. The back support of claim 6 wherein said loops are elastic.

10. The back support of claim 1, expressly adapted to be worn about the waist of a wearer who is pregnant or otherwise possessed of a protruding abdomen, wherein said strap means is bifurcated into an upper portion and a lower portion, so that said strap means may be disposed to the top and bottom of the protruding abdomen of the wearer.

11. The back support of claim 10 wherein said lower portion of said strap means is configured and dimensioned to at least partially support the protruding abdomen, and said upper portion of said strap means is configured and dimensioned to stabilize the position of the protruding abdomen.

12. The back support of claim 10 additionally including a resiliently elastic cover extending between and connecting said upper and lower portions of said strap means.

13. The back support of claim 1 wherein said strap means is secured at one end thereof to the other end of one of said side Pads and is removably secured at the other end thereof to the other end of the other one of said side pads for releasably connecting said strap means and said other one side pad adjacent the side of the wearer to adjustably fit said back support about the wearer's waist, 14. The back support of claim 13 wherein said strap means is removably secured at both ends thereof to the other ends of said side pads and thus detachable from said side pads.

15. The back support of claim 1 wherein said strap means comprises a pair of strap elements, each said strap element being secured at one end thereof to the other end of a respective one of said side pads and having fastening means at the other end thereof for releasably connecting said strap elements together to adjustably fit said back support about the wearer's waist.

16. The back support of claim 15 wherein said back support is of unitary one-piece construction.

17. The back support of claim 1 wherein said strap means is resiliently elastic.

18. A back support adapted to be worn about a person's waist comprising:
(A) a resiliently compressible, flexible, fabric-coated elongate foam back pad configured and dimensioned to be positioned against the wearer's lower back when said back support is worn, said back pad including a fabric cover filled with a resiliently compressible, flexible, substantially homogeneous filler material and having stitching therethrough which compresses said filler material in different areas to different degrees, said stitching defining first areas of greater stiffness adjacent each side of said back pad and a plurality of second areas of lesser stiffness intermediate said first areas, whereby said back pad has greater thickness and less firmness in said second areas and less thickness and greater firmness in said first areas.;
(B) a pair of resiliently compressible, flexible, elongate foam side pads configured and dimensioned to be positioned against the wearer's sides when said back support is worn, each of said side pads being secured at one end to a respective end of said back pad; and
(C) at least one elastic ring disposed on each side pad intermediate the ends thereof and slidable along the length thereof for adjusting the bulk of said side pad to fill the portion of the wearer's waist intermediate the rib cage and the hips and thereby provide support thereto when the wearer lies on his/her side on a generally flat surface; and
(D) resiliently elastic, flexible strap means for releasably operably connecting said side pads together to adjustably fit said back support about the wearer's waist.

19. The back support of claim 18, expressly adapted to be worn about the waist of a wearer who is pregnant or otherwise possessed of a protruding abdomen, wherein said strap means is bifurcated into an upper portion and a lower portion, so that said strap means may be disposed to the top and bottom of the protruding abdomen of the wearer; said lower portion of said strap means being configured and dimensioned to at least partially support the protruding abdomen, and said upper portion of said strap means being configured and dimensioned to stabilize the position of the protruding abdomen; and additionally including a resiliently elastic cover extending between and connecting said upper and lower portions of said strap means.

20. A back support adapted to be worn about a person's waist comprising:
(A) a resiliently compressible, flexible, elongate back pad configured and dimensioned to be positioned against the wearer's lower back when said back support is worn, said back pad being filled with a resiliently compressible, flexible filler material and having stitching therethrough which compresses said filler material in different areas to different degrees; said back pad having an egg crate inner surface facing away form the wearer and a generally smooth outer surface facing the wearer;
(B) a pair of resiliently compressible, flexible, elongate side pads configured and dimensioned to be positioned against the wearer's sides when said back support is worn, each of said side pads being secured at one end to a respective end of said back pad; and
(C) flexible strap means for releasably operably connecting said side pads together to adjustably fit said back support about the wearer's waist.

21. A back support adapted to be worn about a person's waist comprising:
(A) a resiliently compressible, flexible, elongate back pad configured an dimensioned to be positioned against the wearer's lower back when said back support is worn, said back pad being filled with a resiliently compressible, flexible filler material and having stitching therethrough which compresses said filler material in different areas to different degrees;
(B) a pair of resiliently compressible, flexible, elongate side pads configured and dimensioned to be positioned against the wearer's sides when said back support is worn, each of said side pads being secured at one end to a respective end of said back pad; and
(C) at least one loop disposed on each side pad intermediate the ends thereof for adjusting the bulk of said side pad to fill the portion of the wearer's waist intermediate the rib cage and the hips and thereby provide support thereto when the wearer lies on his/her side on a generally flat surface; and
(D) flexible strap means for releasably operably connecting said side pads together to adjustably fit said back support about the wearer's waist.

22. The back support of claim 21 wherein each of said loops is removable from its respective side pad.

23. The back support of claim 21 wherein each of said loops is slidable along the length of its respective side pad for adjusting the distribution of the bulk thereof.

24. The back support of claim 21 wherein said loops are elastic.

* * * * *